US005866719A

United States Patent [19]

Desantis et al.

[11] Patent Number: 5,866,719

[45] Date of Patent: Feb. 2, 1999

[54] PROCESS FOR THE PURIFICATION OF AN AMINOALCOHOL

[75] Inventors: Nicola Desantis; Franco Fedeli, both of Ceriano Laghetto, Italy

[73] Assignee: Dibra S.p.A., Italy

[21] Appl. No.: 984,086

[22] Filed: Dec. 3, 1997

[30] Foreign Application Priority Data

Dec. 4, 1996 [IT] Italy .................................. MI96A2546

[51] Int. Cl.[6] .................................................. C07C 213/00

[52] U.S. Cl. ............................................ 564/497; 564/507

[58] Field of Search ..................................... 564/497, 507

[56] References Cited

U.S. PATENT DOCUMENTS 5,053,545 10/1991 Marman et al. ........................ 564/495

*Primary Examiner*—Peter O'Sullivan

*Attorney, Agent, or Firm*—Nixon & Vanderhye

[57] ABSTRACT

The present invention relates to a process for the preparation of 2-amino-1,3-propanediol, having a content of organic impurities lower than 0.1% and inorganic impurities lower than 0.05%, comprising the following steps:

a) formation of a 2-amino-1,3-propanediol salt with an acid;

b) crystallization of the salt resulting from step a) from an aqueous or a hydro-organic mixture with a solvent selected from the group consisting of an alcohol of general formula R—OH, wherein R is a $C_1$–$C_6$ straight or branched alkyl chain, and a mono($C_1$–$C_3$)alkylether of the ($C_3$–$C_7$)alkylcellosolve group;

c) elution of the free base by using ion exchangers to give an aqueous solution of said base;

d) precipitation or crystallization of the solid 2-amino-1,3-propanediol from a solvent as defined in step b).

16 Claims, No Drawings

PROCESS FOR THE PURIFICATION OF AN AMINOALCOHOL 2-amino-1,3-propanediol of formula (I), known as serinol, is widely used as building-block in the synthesis of non-ionic iodinated X-ray contrast media.

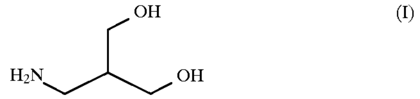

(I)

Great attention has been paid on its synthetic preparation, since the cost of such products is quite high, while its purification has been considered less interesting.

The main industrial application of this product relies on the synthesis of many non-ionic X-ray contrast media, particularly (S)-N,N'-bis-[2-hydroxy-1-(hydroxymethyl) ethyl]-5-[(2-hydroxy-1-oxopropyl)amino]-2,4,6-triiodo-1, 3-benzenedicarboxamide, known with the international denomination of Iopamidol (The Merck Index, XI Ed., page 799, n°4943).

Physicians and authorities which grant drug market authorizations, require drugs with very low level of impurities in order to limit the number of side-effects experienced by patients.

As far as iodinated contrast agents are concerned, particular care must be paid since the total amount of administered product is much higher than other drugs. As a matter of example, the injected contrast agent dose can reach or exceed 150 g.

The high purity level of the compound of formula (I) is extremely important in order to avoid by-products and assure high purity standards in the final products.

In literature there are various purification methods of compound (I) such as vacuum-distillation, which is the most widely used (for instance U.S. Pat No. 5,053,545, U.S. Pat. No. 4,221,740), and a purification process which provides for the use of styrene-divinylbenzene resins, such as XAD-2 (see U.S. Pat. No. 5,432,868).

Beyond serinol, two of its salts are commercially supplied, that's to say hydrochloride and oxalate which show a better stability and handling, compared to the free base. The synthesis and the crystallization of these salts has been already described in some patents (for instance EP 348223, U.S. Pat. No. 5,053,545). The purity reported by manufacturers is 98%, therefore unsatisfactory.

As already known in literature (F. Uggeri et al., Journal of Chromatography, 432, 1988) the main organic by-products of compound (I), whose purification is the object of this invention, are: N-methyl-1-amino-2,3-propanediol, ethanolamine, 2,3-diaminopropanol, 1,3-diaminopropanol, glycerine and 2-aminopropanol, but also some inorganic impurities, the structural isomer of compound of formula (I), that's to say 3-amino-1,2-propanediol, known as isoserinol, must be considered.

According to the type of industrial synthesis of the compound of formula (I), percentages of the impurity main components can remarkably differ.

Therefore it is important to have available selective purification processes for said impurities.

This invention refers to a process for the purification of 2-amino-1,3-propanediol to obtain a product characterized by a content of organic impurities lower than 0.1% and inorganic impurities lower than 0.05% comprising the following steps:

a) formation of a 2-amino-1,3-propanediol salt with an acid, preferably hydrochloric acid or oxalic acid;

b) crystallization of the salt formed in step a) from an aqueous or, alternatively, hydro-organic mixture with a solvent selected from the group consisting of an alcohol of formula R—OH, wherein R is a ($C_1$–$C_6$) straight or branched alkyl chain, a mono($C_1$–$C_3$)-alkylether of the ($C_3$–$C_7$)alkylcellosolve group;

c) elution of the free base by using ion exchangers to give an aqueous solution of said base;

d) formation of the solid 2-amino-1,3-propanediol by precipitation or crystallization from alcohols of formula R—OH.

Crystallization of salts formed in step a) can be carried out in an aqueous or hydro-organic solution and particularly preferred are the alcohols of formula R—OH selected from the group consisting of methanol, ethanol, propanol, isopropanol, butanol, 2-butanol and t-butanol and 2-methoxyethanol.

Particularly useful are the crystallization techniques of the already known hydrochloride and neutral oxalate of serinol, which are going to be illustrated in detail, since they can give directly marketable products.

We have also found out that obtaining the free base from these salts according to step c), by using $H^+$ or $Na^+$ form cation exchangers, gives a free base furtherly purified by the chromatographic action carried out by the same resins.

This technique is highly innovative with respect to the chemical methods using an alkaline or alkaline-earth base to free these salts, in particular sodium hydroxide, potassium hydroxide and calcium hydroxide, since the salt conversion to free base is quantitative and no traces of inorganic impurities are detected in the resulting product. The filtration step of the inorganic salt (for instance calcium oxalate, sodium chloride, potassium chloride), which causes product losses due to the troublesome washing of the panel of said salt on the filter, is thus avoided.

The use of the process of this invention is particularly advantageous, on an industrial scale, even for the removal of the colour from the raw solutions and the easy automation of the process by means of a potentiometer, conductimeter and refractometer equipped with flow cells.

The preferred cation exchangers are selected from the group consisting of gel or macroporous polystyrene-based exchangers having sulphonic acid groups. For example: C 20 MB (Duolite), Amberlite® IR 120 (Rhom & Haas), Amberjet® 1200 (Rhom & Haas) or alternatively C 100 E (Purolite) or C 350 MB (Dow). In any case analogous cationic exchangers by different manufacturers can be used.

The compound of formula (I) is recovered through elution with aqueous ammonia, in particular the use of 4.7% aqueous ammonia allows the elimination of inorganic impurities. The exceeding ammonia is easily removed through evaporation before step d).

When necessary the reaction can be monitored through pH and so it is very easy to discard the most impure fractions.

Strong anion exchangers can be used to produce a free base from a crude solution containing a mixture of inorganic or organic acid which can be water-insoluble and able to salify serinol, therefore having a different action from that performed by cation exchangers. This method, even though it excludes a chromatographic action on the compound of formula (I), gives a free base in a single step, exploiting the higher basicity of tertiary amines of the anion exchanger compared to serinol.

The preferred anion exchangers are selected from the group consisting of strong anion exchangers such as gel or macroporous polystyrene- based exchangers with diethylammonium or dimethylammonium groups.

For example: Amberlite® IRA 420 or other types with analogous features (for instance A 400 Purolite, SA 12 A Diaion, SBR-P Dowex).

Also for this process, control systems, such as potentiometer, conductimeter and refractometer, can be used making the process more easily exploitable and automated.

As already cited the methods of the literature teach vacuum- distillation to give solid serinol, we have found out a simple and effective method to attain the same aim, without submitting the product to a prolonged damaging thermal treatment.

After elution of the free base through ion exchangers, an aqueous solution of the compound of formula (I) is obtained which, after concentration, can cause the crystallization or precipitation of the free base.

If water content is lower than 3% a precipitation occurs, otherwise it is more profitable to operate with a maximum water content of 20% according to the type of solvent used for crystallization.

Particularly preferred are the crystallization solvents selected from the group consisting of ethanol, 2-butanol, n-butanol, t-butanol, isobutanol, pentanol, isopentanol.

The method comprises a precipitation at temperatures ranging from −5° C. to 30° C. according to the solvent used.

When the impurities are mainly inorganic or the compound of formula (I) is contaminated by a salt of 5-amino-2,4,6-triiodoisophthalic acid, this invention also refers to a process for the purification of 2-amino-1,3-propanediol with same previous characteristics of purity, said process comprising the following steps:

a)' preparation of an aqueous solution of 2-amino-1,3-propanediol and elution of said solution on ion exchangers under the previously described conditions to give an aqueous solution of 2-amino-1,3-propanediol;

b)' precipitation or crystallization of solid 2-amino-1,3-propanediol from an alcohol of formula R—OH, under the previously described conditions.

When the organic impurities in 2-amino-1,3-propanediol amount to 2% and are the only ones present, this invention also refers to a process for the purification of a product with the same previous characteristics of purity, said process comprising only the step of precipitation or crystallization of the compound of formula (I) from an alcohol of formula R—OH, according to the previous conditions.

The analytical methods used to evaluate the quality of aminopropanediols is reported in the previously cited publication (F. Uggeri et al., Journal of Chromatography, 432, 1988).

In order to have a clearer and simpler view of this invention, a list of the salts which can be used for the compound (I) is given below, while the methods are illustrated in the examples.

1) Serinol neutral oxalate

The preparation of neutral salt with oxalic acid is known; it can be easily crystallized from water by working with solutions having a concentration ranging from 12.5% to 90% (w/w) in water.

The resulting yields are higher than 80% with a high purity. In fact, salts with a content of organic impurities lower than 0.3% and the practically complete removal of inorganic impurities, are obtained.

In addition, the structural isomer isoserinol is totally removed in a selective way with this method. The weight ratio between water and the salt ranges between 1:0.5 and 1:10, according to the desired purification level.

As already cited, we have found out that the use of an organic solvent mixed with water during crystallization can analogously reduce by-products and overcomes the problem connected to the troublesome filtration of the salt crystallized from water.

In particular purifying activity is higher with respect to known and unknown by-products with lipophilic characteristics such as secondary and tertiary amines which can be present and the capacity of removing the isomer, isoserinol, is kept in a complete way or within residual values of 0.1%. The organic solvents used are the alcohols of general formula R—OH, above described, as well as the particularly preferred alcohols and monoalkyether glycols.

The water content in the case of the neutral oxalate of serinol in the hydro-organic precipitation mixtures can range from 0% to 95%. The weight ratio between the neutral oxalate of compound (I) and the solvent can range between 1:1 to 1:10 parts by weight.

2) Serinol hydrochloride

Serinol is easily salified with hydrochloric acid. The salt is not crystallizable from water due to its high solubility.

Different patents describe the preparation of serinol hydrochloride as crude final product, therefore the crystallization of such salt is a remarkable advantage, being the same salt a product commercially supplied.

Some patents, such as U.S. Pat. No. 5,053,545, illustrate hydrochloride as synthetic intermediate which is converted into free base through reaction of the salt with sodium hydroxide.

Other patents, such as EP 348223, give examples of crystallization of salts using low molecular weight alcohols for serinol.

The salt can be obtained through the action of aqueous hydrochloric acid in the final step or, alternatively, when this technique is used for purification, the free base can be dissolved in organic solvents and therefore hydrogen chloride is added up to saturation.

Salt crystallization, according to the method of this invention, is performed through hydro-organic mixtures in which water content ranges, for serinol hydrochloride, from 0% to 10% (w/w) while the salt/solvent ratio can range from 1:0.5 to 1:10 (w/w) at a crystallization temperature ranging from −5° C. to 15° C.

Preferred organic solvents are ethanol and 2-methoxyethanol.

The following examples are intended to illustrate the best experimental conditions to carry out the process of this invention.

EXAMPLE 1

Purification of serinol neutral oxalate.

300 g of crude serinol neutral oxalate containing 2% of organic by-products and 8% of inorganic by-products (sodium chloride, sodium sulfate) are diluted in 600 g of water at 80° C. The solution is kept at 80° C. for 1 h. 10 g of active carbon are added and the mixture was kept under stirring at the same temperature for 1 h. Then the mixture is filtered at 80° C. and carbon is removed by washing with 120 g of water preheated to 80° C. Then the solution is slowly cooled to 30° C. in 2 h then to 0°–1° C., keeping the temperature for 2 h. It is filtered under vacuum (20 mmHg) and washed with 300 g of 50% aqueous methanol (w/w) precooled at 0°–1° C. After drying at 70° C. for 12 h at 12 mmHg 250 g of dry product were obtained.

Elution of the free base

The resulting product is dissolved in water thus giving a 15%-weight solution. The solution is percolated on 1200 mL of $H^+$-form cation exchanger Amberjet® 1200, obtained by washing the resin at a neutral pH.

Serinol is eluted with 1200 mL of 4.7% aqueous ammonia at appr. 2 BV/h. The resin is washed to neutral pH with deionized water (approx. 2L). The resulting solution is evaporated to a residue then dissolved with 200 g of anhydrous 2-butanol and evaporated to a residue through under vacuum concentration (7 mmHg) to give a residue with a water content <0.3%.

Precipitation of the free base

The residue is dissolved with 1150 g of 2-butanol then cooled to −3° C., the temperature is kept for 3 h. Serinol is filtered and washed with 120 g of 2-butanol precooled at 0° C., dried at 30° C. under vacuum (3 mmHg) for 12 h to give 240 g of dry serinol.

Total yield 70%. Total organic by-products 0.05% ashes-free.

EXAMPLE 2

Alternative to Example 1 using methanol as solvent.

300 g of serinol neutral oxalate containing 1% of organic by-products are dissolved in 1000 g of water at 80° C. The solution is decolorized with 1.5 g of active carbon and filtered at 80° C. then cooled to 60° C. and 1000 g of anhydrous methanol are added. The temperature is kept to 17° C. for 5 h. The resulting product is filtered and washed with 150 g of methanol then dried at 60° C. (12 mmHg) for 12 h in order to give 285 g of dry product. The free base is obtained according to Example 1.

Free base crystallization

The residue is dissolved with 1150 g of 5%-water 2-butanol. Then it is cooled to −3° C., and the temperature is kept for 3 h. The product is filtered and washed with 120 g of 2-butanol precooled at 0° C., dried at 30° C. under vacuum (3 mmHg) for 12 h.

Total yield 90%. Total organic by-products 0.06% ashes-free.

EXAMPLE 3

Alternative to Example 1 using ethanol as solvent.

300 g of serinol neutral oxalate containing 1.5% of organic by-products and 3% of inorganic by-products are dissolved in 800 g of water at 80° C.

The solution is decolorized with 1.5 g of active carbon and filtered at 80° C., then cooled to 60° C. and 800 g of anhydrous ethanol are added. The temperature is lowered to 17° C. for 5 h. The resulting product is filtered and washed with 200 g of 95% methanol (w/w), then dried at 60° C. (12 mmHg) for 12 h to give 285 g of dry product. The free base is obtained according to the Example 1 using n-butanol as anhydrification solvent.

Free base crystallization

The residue is dissolved with 1000 g of n-butanol (water content 5%) then cooled to −3° C., and the temperature is kept for 3 h. Serinol is filtered and washed with 120 g of n-butanol precooled at 0° C., dried at 30° C. under vacuum (3 mmHg) for 12 h.

Total yield 90%. Total organic by-products 0.06% ashes-free.

EXAMPLE 4

Purification of serinol hydrochloride.

300 g of crude serinol hydrochloride containing 1% of organic by-products comprising 0.2% of isoserinol and 0.3% of methylserinol are dissolved in 450 g of 2-methoxyethanol at 90° C. The resulting solution is gradually cooled to 15° C. and the temperature is kept for 2 h. The precipitate is filtered and washed with 40 g of 2-methoxyethanol precooled at 0° C. First crop yield: 90%.

Mother liquors are concentrated to 750 g and the second crop is precipitated by repeating the procedure. Second crop yield: 10%.

285 g of product between the first and the second crop are given and dried at 60° C. (12 mmHg) for 12 h. Hydrochloride is converted into free base following the procedure of Example 1.

Total yield 87%. Total organic by-products 0.1% ashes-free.

EXAMPLE 5

Serinol Purification containing 5-amino-2,4,6-triiodoisophthalic acid.

200 g of serinol containing 10% of 5-amino-2,4,6-triiodoisophthalic acid, 10% of inorganic substances and 0.4% of organic impurities are dissolved in 2000 g of water. The solution is percolated on 1200 mL of Na+−form cation exchanger C 350 MB, obtained by washing the bed up to neutral pH. Serinol is eluted with 1200 mL of 4.7% (w/w) aqueous ammonia at approx. 2 BV/h. The resin is washed to neutral pH with deionized water (approx. 2L). The resulting solution is concentrated to a residue and dissolved with 400 g of iso-butanol.

Precipitation of the free base

The residue is dissolved with 1000 g of iso-butanol then cooled to −3° C., and the temperature is kept for 3 h. Serinol is filtered and washed with 100 g of solvent precooled at 0° C., dried at 30° C. under vacuum (3 mmHg) for 12 h.

Total yield 85%. Total organic by-products 0.08% ashes-free.

EXAMPLE 6

Alternative to Example 4.

300 g of serinol salified with hydrochloric acid and 5% of sodium sulfate and 1.0% of organic impurities are dissolved in 3000 g of water. The solution is percolated on 2000 mL of anion exchanger IRA 420 and the bed is washed up to neutral pH, at approx. 2 BV/h. Serinol is recovered reducing the eluate to a residue of approximately 220 g with 10% (w/w) of water.

Precipitation of the free base

The residue is dissolved with 1000 g of iso-pentanol. Then it is cooled to −3° C., and the temperature is kept for 3 h. Serinol is filtered and washed with 100 g of isopentanol precooled at 0°, dried at 30° C. under vacuum (3 mmHg) for 12 h.

Total yield 85%. Total organic by-products 0.08% ashes-free.

EXAMPLE 7

Free base crystallization.

200 g of serinol containing 1% of inorganic substances and 1% of organic impurities are dissolved in 600 g of 10%-water iso-pentanol heating to 40° C. if desired. Then it is cooled to −3° C., and the temperature is kept for 6 h. Serinol is filtered and washed with 120 g of anhydrous solvent precooled at 0° C., dried at 30° C. under vacuum (3 mmHg) for 12 h.

Total yield 78%. Total organic by-products 0.01% ashes-free.

EXAMPLE 8

Preparation of Iopamidol using the serinol purified as previously described 680 g of S-(-)-5-((2-acetyloxy)-1-oxopropyl)amino)-2,4,6-triiodo-1,3-benzendicarboxylic acid dichloride (prepared as described in WO 96/37460) are dissolved in 1360 g of dimethylacetamide at room temperature and after cooling at 15° C. [Solution A ].

181 g of 2-ammino-1,3-propanediol purified with the method described in the previous Example 1 are dissolved in 1360 g of dimethylacetamide and added to the solution A in one hour at 8°–15° C. whilst stirring. The reaction is completed after ten hours at room temperature.

The reaction mixture is concentrated at 100° C. at 10 mbar until 98% of the solvent is distilled.

1700 g of water are added to the residue and the solution is purified using the method described in WO 97/30735. Yield on dry Iopamidol: 94%

Contents of by-products determined with HPLC method (according to the method described in USP XXIII-NF, 1996, V°suppl.)=0.11%.

The by-product N-[2-hydroxy-1-(hydroxymethyl)ethyl]-N'-(2,3-dihydroxypropyl)-5-(2-hydroxy-1-oxopropyl)-2,4,6-triiodo-1,3-benzenedicarboxamide, coming from isoserinol, is under the detection limit.

No presence of other by-products derived from 3-amino-1,2-propanediol are detected (see as ref. Pharmeuropa, 6, 343–345, 19949.

We claim:

1. Process for the preparation of 2-amino-1,3-propanediol, having a content of organic impurities lower than 0.1% and inorganic impurities lower than 0.05%, said process comprising the following steps:

a) formation of a 2-amino-1,3-propanediol salt with hydrochloric acid or oxalic acid;

b) crystallization of the salt resulting from step a) from an aqueous or a hydro-organic mixture with a solvent selected from the group consisting of an alcohol of formula R—OH, wherein R is a $C_1$–$C_6$ straight or branched alkyl chain, and a mono ($C_1$–$C_3$) alkylether of the ($C_3$–$C_7$) alkylcellosolve group;

c) elution of the free base using ion exchangers to give an aqueous solution of said base; and d) precipitation or crystallization of the solid 2-amino-1,3-propanediol from a solvent as defined in step b).

2. Process according to claim 1, in which the crystallization of the salt in step b) is carried out in hydro-organic solution and the solvent is selected from the group consisting of methanol, ethanol, propanol, isopropanol, butanol, 2-butanol, t-butanol and 2-methoxyethanol.

3. Process according to claim 1, in which the elution of the free base in step c) is carried out using $Na^+$ or $H^+$ form cation exchangers.

4. Process according to claim 3, in which the cation exchangers are gel or macroporous polystyrene- based exchangers having sulphonic acid groups.

5. Process according to claim 3, in which 2-amino-1,3-propanediol is recovered through elution with aqueous ammonia.

6. Process according to claim 1, in which the elution of 2-amino-1,3-propanediol is monitored through pH and carried out so that the fractions having the highest content of impurities are discarded.

7. Process according to claim 1, in which the elution of 2-amino-1,3-propanediol in step c) is carried out through the use of strong anion exchangers.

8. Process according to claim 7, in which the anionic exchangers are gel or macroporous polystyrene- based exchangers with diethylammonium or dimethylammonium groups.

9. Process according to claim 1, in which the solvent precipitation of 2-amino-1,3-propanediol of the aqueous solution obtained after step c) is from a solvent when the water content is a maximum 3%, at a temperature ranging between −5° C. and 30° C.

10. Process according to claim 1, in which the crystallization of 2-amino-1,3-propanediol of the aqueous solution obtained after step c) is from a solvent when the water content is a maximum 20%, at a temperature ranging between −5° C. and 30° C.

11. Process according to claim 10, in which the solvent is selected from the group consisting of methanol, ethanol, propanol, isopropanol, butanol, 2-butanol, t-butanol and 2-methoxyethanol.

12. Process for the preparation of 2-amino-1,3-propanediol, having a content of organic impurities lower than 0.1% and inorganic impurities lower than 0.05%, when said impurities are mainly inorganic or said 2-amino-1,3-propanediol is contaminated by a salt of 5-amino-2,4,6-triiodoisophthalic acid, said process comprising the following steps:

a)' preparation of an aqueous solution of 2-amino-1,3-propanediol and elution of said solution on ion exchangers according to step c) in claim 1, to give an aqueous solution of 2-amino-1,3-propanediol;

b)' precipitation or crystallization of solid 2-amino-1,3-propanediol from the solvent according to step d) of claim 1.

13. Process for the preparation of 2-amino-1,3-propanediol, having a content of organic impurities lower than 0.1% and inorganic impurities lower than 0.05%, when the organic impurities amount to 2% and are the only ones present, said process comprising only the step of precipitation or crystallization of 2-amino-1,3-propanediol from the solvent according to step b) of claim 1.

14. Process according to claim 1, in which in order to crystallize 2-amino-1,3-propanediol neutral oxalate from the hydro-organic mixture, the water content ranges between 0% and 95% and the weight ratio between the salt and the mixture ranges from 1:1 to 1:10 parts by weight.

15. Process according to claim 1, in which in order to crystallize 2-amino-1,3-propanediol hydrochloride from the hydro-organic mixture, the water content ranges from 0% to 10%% (w/w), the weight ratio between the salt and the mixture ranges from 1:0.5 to 1:10 parts by weight.

16. Process according to claim 15, in which the organic solvent of the hydro-organic mixture is selected from the group consisting of ethanol and 2-methoxyethanol.

* * * * *